United States Patent
Evans et al.

(10) Patent No.: US 10,376,345 B2
(45) Date of Patent: Aug. 13, 2019

(54) FLOSS DISPENSERS

(71) Applicant: Flosstime Inc., Palo Alto, CA (US)

(72) Inventors: Michael Evans, Palo Alto, CA (US);
Duc Duong, Mountain View, CA (US);
Gregorio Faria, Palo Alto, CA (US);
Thomas Grimm, Napa, CA (US);
Christopher Loew, Palo Alto, CA (US)

(73) Assignee: Flosstime Inc., Palo Alto, CA (US)

( * ) Notice: Subject to any disclaimer, the term of this patent is extended or adjusted under 35 U.S.C. 154(b) by 224 days.

(21) Appl. No.: 14/835,498

(22) Filed: Aug. 25, 2015

(65) Prior Publication Data
US 2016/0051351 A1    Feb. 25, 2016

Related U.S. Application Data

(60) Provisional application No. 62/070,388, filed on Aug. 25, 2014, provisional application No. 62/124,302, filed on Dec. 15, 2014.

(51) Int. Cl.
*A61C 15/04*    (2006.01)

(52) U.S. Cl.
CPC ................. *A61C 15/043* (2013.01)

(58) Field of Classification Search
CPC ....... A61C 15/04; A61C 15/043; A61C 7/306; A61C 15/046; A45D 40/18; Y10T 225/237; Y10T 225/253; Y10T 225/995; Y10T 225/241; B26D 47/0804; B65D 43/22; B65D 51/28
USPC .... 225/1, 38, 42, 52, 89, 10, 11, 34, 15, 14, 225/324, 325; 132/309, 325, 311, 308, 132/324, 310; 83/649
See application file for complete search history.

(56) References Cited

U.S. PATENT DOCUMENTS

| | | | |
|---|---|---|---|
| 1,171,177 A | 2/1916 | de l'Eau | |
| 1,260,011 A | 3/1918 | Muchow | |
| 2,967,651 A * | 1/1961 | Zackheim | A47F 13/04 225/80 |
| 3,830,246 A | 8/1974 | Gillings | |
| 3,853,134 A * | 12/1974 | McCord | A46B 15/0071 132/309 |
| 3,894,550 A | 7/1975 | Eaton | |
| 4,836,415 A | 6/1989 | Grussmark | |

(Continued)

FOREIGN PATENT DOCUMENTS

WO    WO 2001078623 A1    10/2001

OTHER PUBLICATIONS

Dispenser9, "Toothpaste Dispenser & Dental Floss & Toothbrushes (3 in 1)" [online], uploaded on Jun. 29, 2009 (Jun. 29, 2009), https://www.youtube.com/watch?v= klu9ilmu1yA.

(Continued)

*Primary Examiner* — Ghassem Alie
(74) *Attorney, Agent, or Firm* — Jinn Su

(57) ABSTRACT

Floss dispensers are described. In one embodiment, a floss dispenser includes a housing and a feeder coupled to the housing. The feeder may be configured to feed a length of floss from a spool of floss. The floss dispenser also includes a spout formed in the housing. The spout may have a cutter entry and a cutter exit. The floss dispenser also includes a cutter coupled to the housing. The cutter may be coupled to the housing between the cutter entry and the cutter exit. The spout may be configured to guide the length of floss to the cutter.

13 Claims, 10 Drawing Sheets

(56) References Cited

U.S. PATENT DOCUMENTS

| | | | | |
|---|---|---|---|---|
| 4,991,755 | A | 2/1991 | Grussmark | |
| 5,054,674 | A * | 10/1991 | Fortman | A47K 1/09 225/42 |
| 5,076,423 | A | 12/1991 | Russack | |
| 5,170,809 | A | 12/1992 | Imai et al. | |
| 5,184,959 | A | 2/1993 | Oryhon et al. | |
| 5,282,316 | A * | 2/1994 | Anderson | B26B 5/006 30/125 |
| 5,335,798 | A | 8/1994 | Bonwell et al. | |
| 5,400,839 | A | 3/1995 | Cravett | |
| 5,590,471 | A * | 1/1997 | Wiezenthal | A61F 15/02 30/294 |
| 5,613,508 | A * | 3/1997 | Bushman | A61C 15/046 132/325 |
| 5,629,527 | A | 5/1997 | Levitt et al. | |
| 5,645,206 | A * | 7/1997 | Ippisch | A61C 15/043 132/322 |
| 5,826,594 | A | 10/1998 | Sokal | |
| 5,924,429 | A * | 7/1999 | Morando | A46B 5/0095 132/309 |
| 6,009,886 | A | 1/2000 | Labranche et al. | |
| 6,832,916 | B2 | 12/2004 | Collopy | |
| 8,015,982 | B2 * | 9/2011 | Wilkinson | A45D 44/18 132/309 |
| 8,033,428 | B1 | 10/2011 | McEwin | |
| 8,358,203 | B1 | 1/2013 | Perry | |
| 8,550,299 | B2 | 10/2013 | Lohmann | |
| 2003/0017874 | A1 | 1/2003 | Ye et al. | |
| 2008/0257377 | A1 * | 10/2008 | Burrows | A61C 15/043 132/322 |
| 2010/0275449 | A1 * | 11/2010 | Collard | B26B 5/00 30/278 |
| 2012/0167912 | A1 | 7/2012 | Booker | |
| 2012/0171657 | A1 | 7/2012 | Ortins et al. | |
| 2013/0316070 | A1 * | 11/2013 | Patel | A61C 15/046 427/2.29 |
| 2015/0245893 | A1 * | 9/2015 | Kelchlin | A61C 15/043 242/588.6 |
| 2016/0067020 | A1 * | 3/2016 | Hintz | B65D 51/28 132/325 |

OTHER PUBLICATIONS

Marcelmbv, "Dental Floss Dispenser" [online], uploaded on Mar. 15, 2007 (Mar. 15, 2007), https://www.youtube.com/watch?v=wWHacUNkCxM.

TOYT, "The TOYT Mountable Dental Floss Dispenser" [online], uploaded on Feb. 17, 2014 (Feb. 17, 2014), https://www.youtube.com/watch?v=yO_VgLPKgR4.

PCT application PCT/US2015/046794, Feb. 16, 2016 ISR/WO.

* cited by examiner

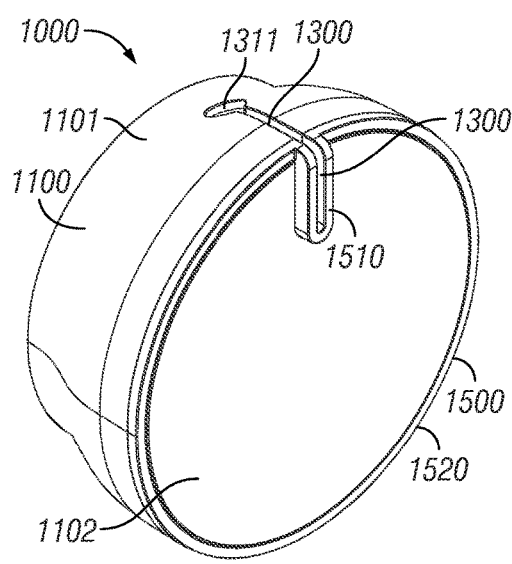
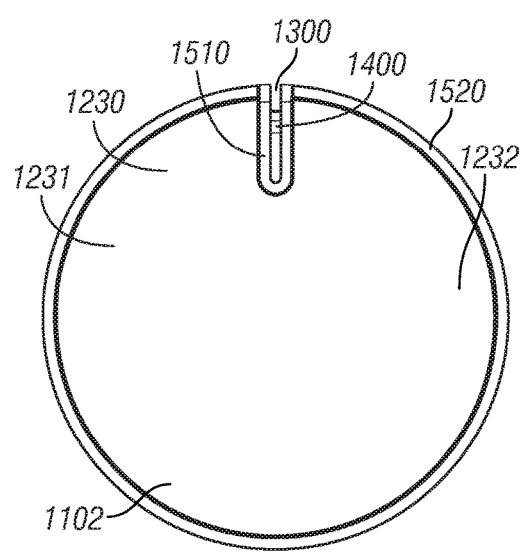
FIG. 1A  FIG. 1B
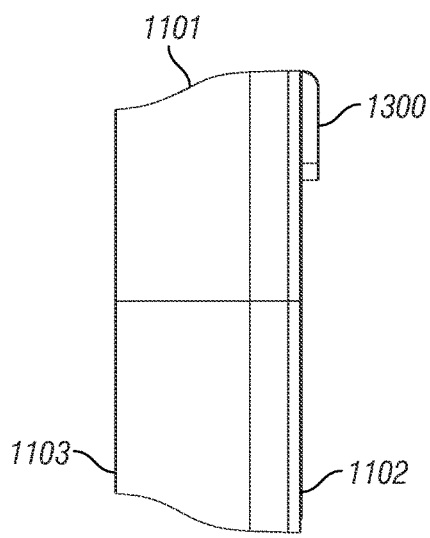
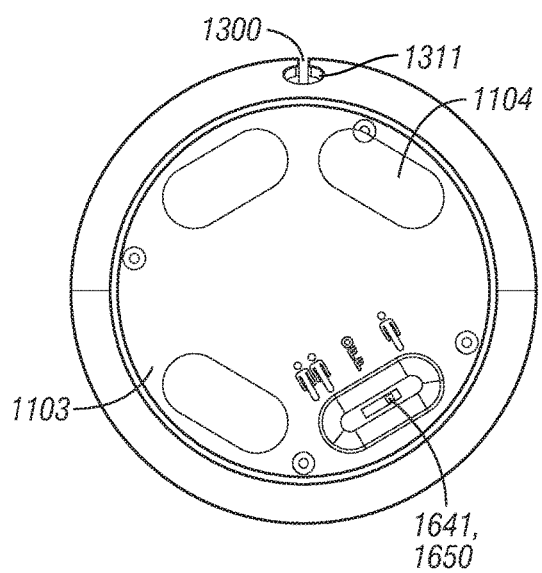
FIG. 1C  FIG. 1D

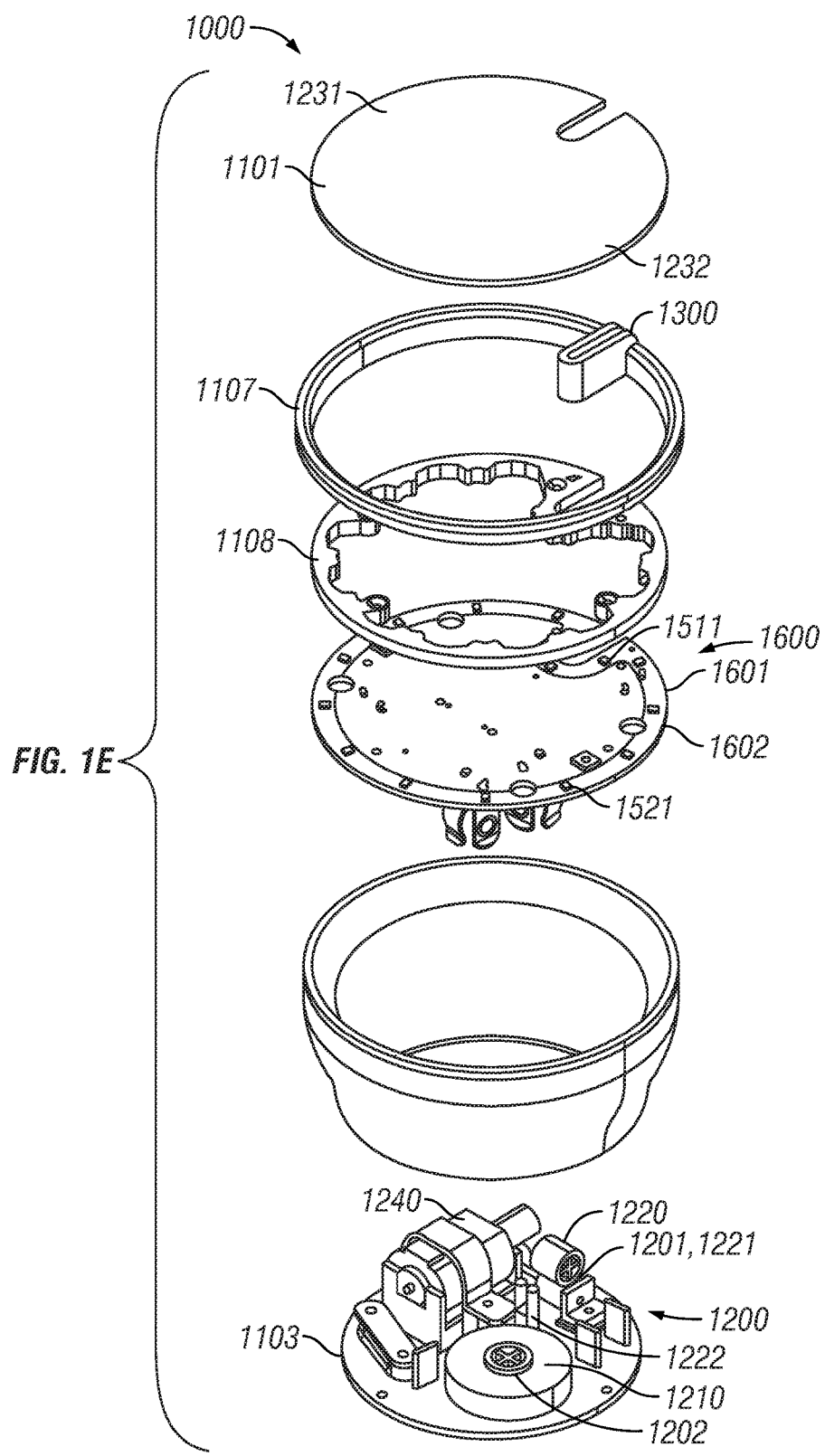

025
FLOSS DISPENSERS

CROSS-REFERENCE TO RELATED APPLICATIONS

This application claims the benefit of U.S. provisional applications Ser. No. 62/070,388, filed Aug. 25, 2014, and Ser. No. 62/124,302, filed Dec. 15, 2014. These applications are hereby incorporated by reference in their entireties.

BACKGROUND

Flossing is important to oral hygiene. However, flossing may be neglected, for a variety of reasons.

People may not floss as often as they need to. People may not be flossing because they do not see the floss. People may not be flossing because they feel it is too much trouble to get the floss. People may not be flossing because they feel flossing is boring or troublesome.

People may not floss as long as they need to. People may be flossing for a shorter time than they believe they are flossing.

What is needed is a device which will facilitate flossing.

SUMMARY

Floss dispensers are described. In one embodiment, a floss dispenser includes a housing and a feeder coupled to the housing. The feeder may be configured to feed a length of floss from a spool of floss. The floss dispenser also includes a spout formed in the housing. The spout may have a cutter entry and a cutter exit. The floss dispenser also includes a cutter coupled to the housing. The cutter may be coupled to the housing between the cutter entry and the cutter exit. The spout may be configured to guide the length of floss to the cutter.

In another embodiment, a floss dispenser includes a housing and a reminder display. The reminder display may include a plurality of reminder lights coupled to the housing. The reminder lights may be configured to display a reminder to floss to a user. The floss dispenser also includes a timer connected to the reminder display. The timer may be configured to determine whether a predetermined period of time has passed since the user last flossed.

BRIEF DESCRIPTION OF THE DRAWINGS

FIGS. 1A-1F show one embodiment of a floss dispenser 1000. FIGS. 1A-1D show perspective, front, side, and back views, respectively, of floss dispenser 1000. FIG. 1E shows a front exploded view of floss dispenser 1000. FIG. 1F shows a back exploded view of a portion of floss dispenser 1000.

FIG. 2A shows an enlarged front view of one embodiment of spout 1300 and cutter 1400. FIGS. 2B-2C show enlarged front views of two embodiments of guide walls 1314 and cutter 1400.

DESCRIPTION

Figure 1F:
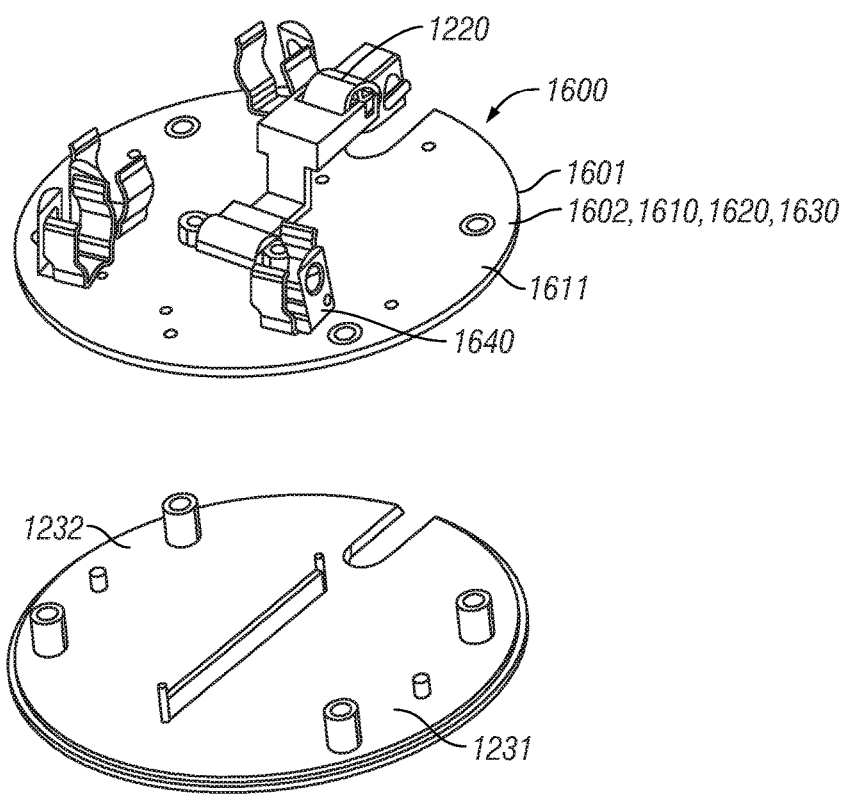

FIGS. 1A-1F show one embodiment of a floss dispenser 1000. FIGS. 1A-1D show perspective, front, side, and back views, respectively, of floss dispenser 1000. FIG. 1E shows a front exploded view of floss dispenser 1000. FIG. 1F shows a back exploded view of a portion of floss dispenser 1000.

Floss dispenser 1000 facilitates flossing. Floss dispenser 1000 may include a housing 1100, a feeder 1200, a spout 1300, and a cutter 1400.

Housing 1100 may include a top 1101, a front 1102, and a back 1103. Housing 1100 may be round or circular to resemble a clock and/or a mouth. Front 1102 of housing 1100 may be round or circular to resemble a face of a clock and/or a mouth. Housing 1100 may have a frustoconical shape. Front 1102 may have a diameter greater than back 1103 of housing 1100. Housing 1100 may be configured so that when housing 1100 is mounted to a mirror, housing 1100 combined with a reflection of housing 1100 resembles an hourglass. Alternatively, housing 1100 may be oval, rectangular, square, or any other suitable shape.

Housing 1100 may include a mount 1104. Mount 1104 may be coupled to back 1103 of housing 1100 and/or any other part of housing 1100. Mount 1104 may include any one or any combination of a microsuction tape, a suction cup, an adhesive tape, a keyhole slot, a hook, or any other suitable coupling device. Mount 1104 may be configured to couple housing 1100 to a vertical surface and/or a horizontal surface. For example, mount 1104 may be configured to couple housing 1100 to a mirror, a wall, a counter, or a table.

Feeder 1200 is coupled to housing 1100. Feeder 1200 is configured to feed floss. Feeder 1200 may include a feed point 1201. Feed point 1201 is a point from which floss is fed.

Feeder 1200 includes a spool holder 1210 configured to hold a spool of floss. Floss may be pulled from the spool of floss by hand, in which case feed point 1201 may be any point along spool holder 1210. Floss may be fed from the spool of floss by two rollers 1220 which contact each other at a pinch point 1221, in which case feed point 1201 may be pinch point 1221. Feeder 1200 may include a feed sensor 1202 configured to sense when floss has been fed.

Spout 1300 is formed in housing 1100. Spout 1300 may include an opening formed through a wall of housing 1100. Spout 1300 may be elongate or any other suitable shape. Spout 1300 may be at least partially formed in top 1101 and/or front 1102 of housing 1100. Spout 1300 may be vertical. Spout 1300 may extend from top 1101 of housing 1100 to front 1102 of housing 1100 and at least partially down front 1102 of housing 1100. Alternatively, spout 1300 may be formed in any other part of housing 1100. Spout 1300 is configured to guide to cutter 1400 floss fed from feeder 1200.

Spout 1300 may include a floss exit hole 1311. Floss exit hole 1311 may be round, elongate, or any other suitable shape. Floss exit hole 1311 may include at least a portion having a width of approximately 2 mm to 8 mm. Floss exit hole 1311 may be formed with or discrete from spout 1300. Floss exit hole 1311 is configured to allow floss to exit housing 1100.

Spout 1300 includes a cutter entry 1312 and a cutter exit 1313. Cutter entry 1312 may be positioned above cutter exit 1313. Cutter entry 1312 may include guide walls 1314. At least a portion of guide walls 1314 may be any one or any combination of parallel, V-shaped, or any other suitable shape. Guide walls 1314 may be configured to reduce the likelihood that floss will miss or bypass cutter 1400. Guide walls 1314 may include a guard 1315 configured to reduce the likelihood that floss will miss or bypass cutter 1400.

Cutter 1400 is coupled to housing 1100. Cutter 1400 may be coupled between cutter entry 1312 and cutter exit 1313. Cutter 1400 may include a stamped floss cutter. Cutter 1400 may include a blade and/or other suitable cutting device. Cutter 1400 may be manual or powered. Cutter 1400 is configured to cut floss. Cutter 1400 may include a cutter sensor 1402 configured to sense when cutter 1400 has cut floss. Cutter sensor 1402 may include any one or any combination of a switch, a pressure sensor, a motion sensor, or any other suitable sensor.

Spout 1300 may be configured so that floss fed from feed point 1201 will be guided into cutter entry 1312. Spout 1300 may be configured so that floss fed from feed point 1201 may be looped around cutter 1400. For example, spout 1300 may be positioned so that when a length of floss is fed, floss will fall under its own weight into cutter entry 1312 and loop over cutter 1400. As another example, spout 1300 may be positioned so that when a length of floss is fed, spout 1300 will be positioned under at least a portion of the length of floss. As yet another example, spout 1300 may extend from floss exit hole 1311 to cutter entry 1312 so that a length of floss may be pulled by a user from floss exit hole 1311 to cutter entry 1312. Floss may be looped around cutter 1400 by pulling floss from cutter entry 1312 towards cutter exit 1313. Floss may be cut by pulling floss across cutter 1400.

Spout 1300 and/or cutter 1400 may be configured to reduce the likelihood of injury to a user. For example, spout 1300 may be sufficiently narrow to prevent the entry of a finger or other body part. As another example, cutter 1400 may be arranged with a sharp or cutting surface out of reach of a finger or other body part.

Figure 2A:
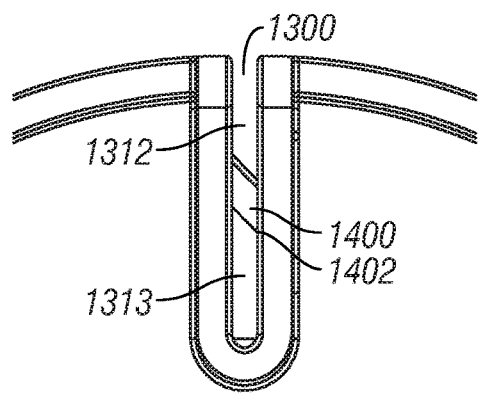
FIGS. 2A-2C show enlarged views of spout 1300 and cutter 1400.
Figure 2B:
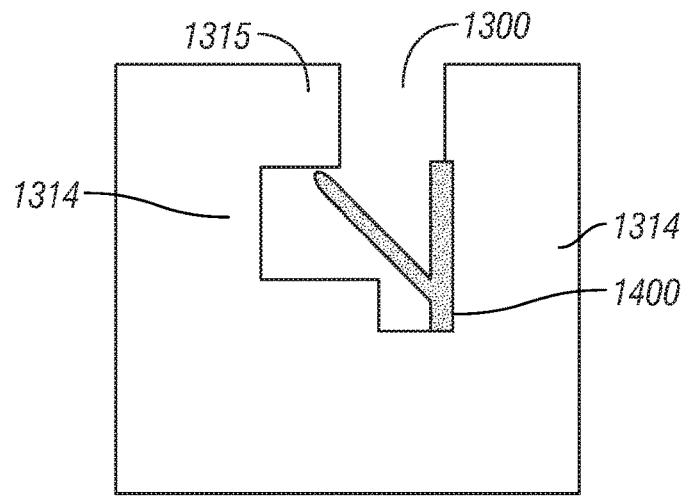
Figure 2C:
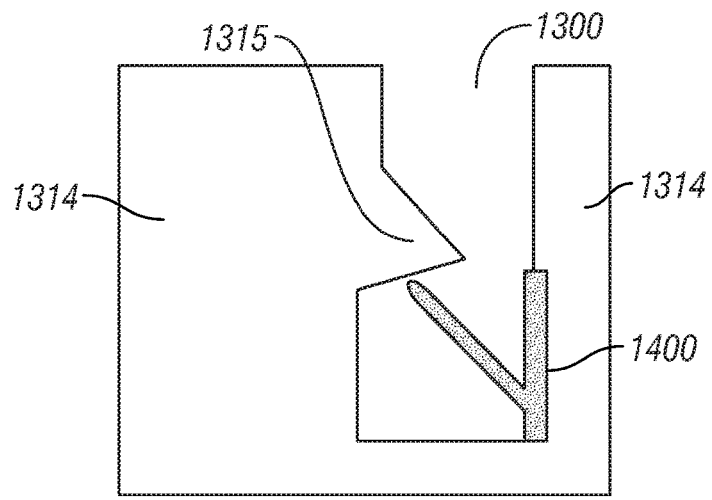
Figure 2D:
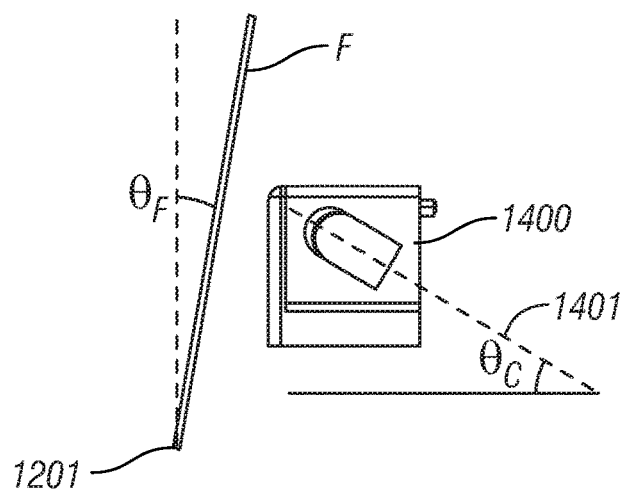
FIG. 2D shows an enlarged cross-sectional side view of cutter 1400.

FIG. 2D shows an enlarged cross-sectional side view of cutter 1400. Floss F may be fed from feed point 1201 in an upward direction, so that floss F may fall under its own weight. For example, floss F may be fed at a feed angle $\Theta_F$ of approximately 10 degrees from vertical, or between approximately 0 degrees and 90 degrees from vertical.

Cutter 1400 may be positioned relative to floss F so that it is capable of cutting floss. For example, cutter 1400 may be positioned with a longitudinal axis 1401 at an cutter angle $\Theta_C$ of approximately 45 degrees to 135 degrees from horizontal.

Cutter 1400 may be positioned higher than feed point 1201. Floss F may have sufficient stiffness to be fed above cutter 1400, before falling under its own weight. This allows a length of floss F to be looped over cutter 1400, and may facilitate the cutting of floss when floss F is pulled downward.

Floss dispenser 1500 may include a display 1500. Display 1500 may include a spout display 1510. Spout display 1510 may include an LCD display and/or any other suitable display.

Spout display 1510 is configured to indicate floss is ready to be cut. Spout display 1510 may indicate for a predetermined period of time, or until the floss has been cut. For example, spout display 1510 may indicate for approximately 3 seconds to 10 seconds after floss has been fed to spout 1300. Spout display 1510 may indicate by any one or any combination of turning on continuously, flashing, "breathing," pulsating, indicating a direction to pull the floss in order to cut the floss, or any other suitable manner.

Spout display 1510 may include one or more spout lights 1511. Spout lights 1511 may include LEDs and/or any other suitable lights. For example, spout lights 1511 may include three LEDs, or one to 10 LEDs. Spout lights 1511 may be configured to display different colors. For example, spout lights 1511 may include RGB LEDs and/or LEDs of different colors. Spout lights 1511 may be coupled to one or more edges and/or guide walls 1314 of spout 1300. Spout lights 1511 may light progressively or in a wave from cutter entry 1312 to cutter exit 1313 to indicate a direction in which floss should be pulled.

Display 1500 may include a reminder display 1520. Reminder display 1520 may include an LCD display and/or any other suitable display. Spout display 1510 and reminder display 1520 may be the same or different displays.

Reminder display 1520 is configured to display reminders to floss. Reminder display 1520 may display a reminder to floss after a predetermined period of time has passed. Reminder display 1520 may display a reminder to floss after a predetermined period of time has passed since a last flossing. For example, reminder display 1520 may display a reminder approximately 22 hours after floss was last fed, or approximately 20 hours after the last reminder if no floss was fed during the last reminder. Reminder display 1520 may display a reminder for a predetermined period of time, or until the floss has been cut. For example, reminder display 1520 may display a reminder for approximately 4 hours. Reminder display 1520 may display a reminder by any one or any combination of turning on continuously, flashing, "breathing," pulsating, or any other suitable manner. Reminder display 1520 may be configured to display reminders to multiple users. For example, reminder display 1520 may indicate for which particular user a reminder is intended. Reminder display 1520 may be configured to display a reminder only when a user is detected in a vicinity of floss dispenser 1000. For example, any one or any combination of a motion sensor, light sensor, or microphone may be used to detect a user in the vicinity of floss dispenser 1000.

Reminder display 1520 may be configured to display a graphical or symbolic representation. For example, reminder display 1520 may be configured to display a reward such as a smile after a user has flossed. As another example, reminder display 1520 may be configured to display a frown as a reminder to floss.

Reminder display 1520 may be configured to indicate a portion of a mouth to be flossed, such as a quadrant of the mouth to be flossed. Reminder display 1520 may be configured to indicate different portions of a mouth to be flossed in sequence, each for a predetermined period of time. For example, reminder display 1520 may be configured to indicate an upper left quadrant, a lower left quadrant, a lower right quadrant, and an upper right quadrant, each for approximately 30 seconds.

Reminder display 1520 may be configured to provide a timer to display a recommended amount of flossing time. Reminder display 1520 may be configured to provide a timer after floss has been fed. Reminder display 1520 may be configured to display an elapsed time and/or a remaining time. For example, reminder display 1520 may be configured to display a recommended flossing time of approximately 2 minutes, which starts counting down after button 1230 is operated. Reminder display 1520 may be configured to display time elapsed since last flossing and/or time remaining until next recommended flossing. Reminder display 1520 may be configured to display the time of last flossing and/or the time of next recommended flossing.

Reminder display 1520 may include one or more reminder lights 1521. Reminder lights 1521 may include LEDs and/or any other suitable lights. For example, reminder lights 1521 may include 12 LEDs, or one to 50 LEDs. Reminder lights 1521 may be coupled to front 1102 of housing 1100 in a circle. Reminder lights 1521 may be coupled to housing 1100 in a square or any other arrangement. Reminder lights 1521 may be coupled along a perimeter of front 1102 of housing 1100. Reminder lights 1521 may be coupled to any other part of housing 1100.

Reminder lights 1521 may be arranged to display a graphical or symbolic representation. For example, reminder lights 1521 may be arranged in a curve that resembles a smile. For a front 1102 of housing 1100 that is circular, reminder lights 1521 may be arranged along a perimeter of a lower half of front 1102 of housing 1100 to resemble a smile. One or more reminder lights 1521 in a smile may be lit more brightly than other reminder lights 1521 in the smile to resemble a "sparkle" in the smile. As another example, reminder lights 1521 may be arranged in a curve that resembles a frown. For a front 1102 of housing 1100 that is circular, reminder lights 1521 may be arranged along a perimeter of an upper half of front 1102 of housing 1100 to resemble a frown. Reminder lights 1521 may be configured to display different colors. For example, reminder lights 1521 may include RGB LEDs and/or LEDs of different colors.

Reminder lights 1521 may be configured to display reminders for multiple users. For example, multiple reminder lights 1521 may be labeled to correspond to different users. As another example, multiple reminder lights 1521 coupled to different parts of housing 1100 may correspond to different users.

Reminder lights 1521 may be configured to indicate a portion of a mouth to be flossed. For example, reminder lights 1521 may be configured to indicate a quadrant of the mouth to be flossed. Reminder lights 1521 may be configured to indicate different portions of a mouth to be flossed in sequence, each for a predetermined period of time. For example, reminder lights 1521 in an upper left quarter of front 1102 of housing 1100 may be used to indicate that an upper left quadrant of the mouth is to be flossed, then reminder lights 1521 in a lower left quarter of front 1102 of housing 1100 may be used to indicate that a lower left quadrant of the mouth is to be flossed, and so on, each quadrant for approximately 30 seconds, for a total of approximately 2 minutes for the entire mouth.

Reminder lights 1521 may be configured to display a recommended amount of flossing time. Reminder lights 1521 may be arranged in a circle or other shape that resembles a face of a clock. Reminder lights 1521 may be configured to display an elapsed flossing time and/or a remaining flossing time. For example, reminder lights 1521 may be configured to display a remaining flossing time of approximately 2 minutes which starts counting down after floss has been dispensed. Reminder lights 1521 may be controlled to resemble a timer counting up or down. For example, all reminder lights 1521 may be turned on, and then turned off one at a time over a period of approximately 2 minutes in a countdown or racetrack fashion, after which all reminder lights 1521 are off. Reminder lights 1521 may be configured to display time elapsed since last flossing and/or time remaining until next flossing.

Floss dispenser 1000 may include electronics 1600. Electronics 1600 may be coupled to housing 1100.

Electronics 1600 may include a timer 1610. Timer 1610 may be coupled to any one or any combination of feed sensor 1202, cutter sensor 1402, or button 1230. Timer 1610 may be configured to determine whether a predetermined period of time has passed since an event. For example, timer 1610 may be configured to determine whether a predetermined period of time has passed since floss was last dispensed and/or since a user last flossed. Timer 1610 may be configured to provide an amount of flossing time.

Timer 1610 may be configured to give visual and/or audio indications. Timer 1610 may be connected to reminder display 1520 and/or reminder lights 1521 to give visual indications. Timer 1610 may be connected to a buzzer or speaker 1611 to give audio indications.

Electronics 1600 may include a display controller 1620. Display controller 1620 is configured to control display 1500. Display controller 1620 may be configured to control spout lights 1511 and/or reminder lights 1521.

Electronics 1600 may include a motor controller 1630. Motor controller 1630 is configured to control a motor. Motor controller 1630 may be configured to provide power to a motor. Motor controller 1630 may be configured to turn on a motor for a desired period of time. Alternatively, motor controller 1630 may be configured to turn on a motor for as long as button 1230 is operated. Motor controller 1630 may be configured to control a speed of a motor. Motor controller 1630 may be configurable to adjust a length of floss fed. For example, motor controller 1630 may be configured to feed approximately 18 inches, or approximately 10 inches to 30 inches of floss.

Electronics 1600 may include a power source 1640. Power source 1640 is configurable to provide power to one or more components of electronics 1600. Power source 1640 may include any one or any combination of a battery, an AC adapter, a solar cell, or any other suitable power source. Power source 1640 may include a power switch 1641. Power switch 1641 is configurable to turn power source 1640 on and off.

Electronics 1600 may include a user selector switch 1650. User selector switch 1650 may allow floss dispenser 1000 to be configurable for use with a single user or two or more users. Power switch 1641 and user selector switch 1650 may be the same switch or different switches.

Electronics 1600 may include a printed circuit board (PCB) 1601. Any one or any combination of timer 1610, display controller 1620, motor controller 1630, power source 1640, or user selector switch 1650 may be connected to PCB 1601. Any one or any combination of timer 1610, display controller 1620, or motor controller 1630 may be implemented in one or more integrated chips 1602.

Figure 3A:
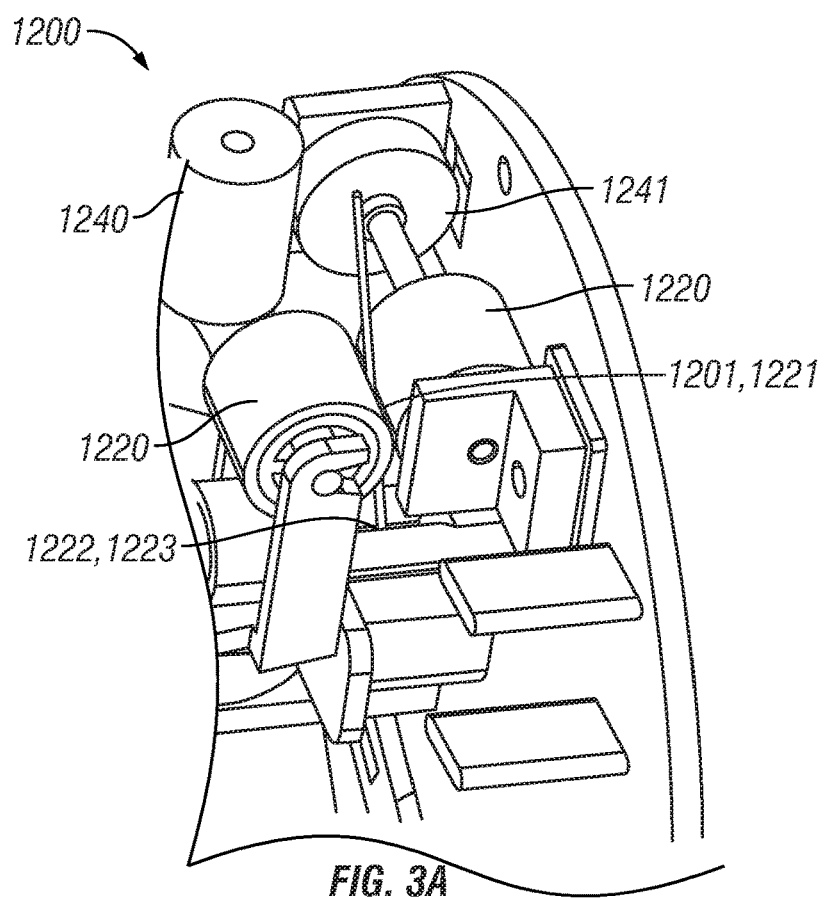
FIG. 3A shows one embodiment of feeder 1200.

FIG. 3A shows one embodiment of feeder 1200. Feeder 1200 is coupled to housing 1100. Feeder 1200 is configured to feed floss.

Feeder 1200 includes a spool holder 1210 configured to hold a spool of floss. The spool of floss may be replaceable. The spool of floss may be part of a replaceable cartridge. Floss may be fed by pulling floss from the spool by hand. Feeder 1200 may include a feed sensor 1202 configured to sense when floss has been fed. Feed sensor 1202 may include any one or any combination of a switch, a pressure sensor, a motion sensor, or any other suitable sensor.

Feeder 1200 may include two or more rollers 1220. Rollers 1220 may be user-powered or electrically-powered.

Two rollers 1220 may contact each other at a pinch point 1221. Rollers 1220 are configured to pull floss from spool holder 1210 and feed floss from pinch point 1221. Rollers 1220 may have a diameter of approximately 5 mm to 15 mm, or approximately 1 mm to 50 mm. Rollers 1220 may have different diameters. Rollers 1220 may rotate at a speed of approximately 400 rpm to 500 rpm, or approximately 10 rpm to 2000 rpm. Pinch point 1221 may be positioned 5 cm or less from floss exit hole 1311.

Figure 3B:
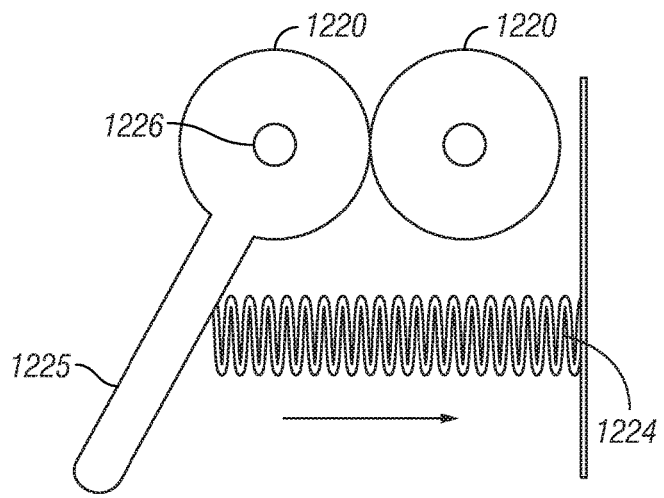
FIGS. 3B-3D show various embodiments of rollers 1220 with a spring 1224.
Figure 3C:
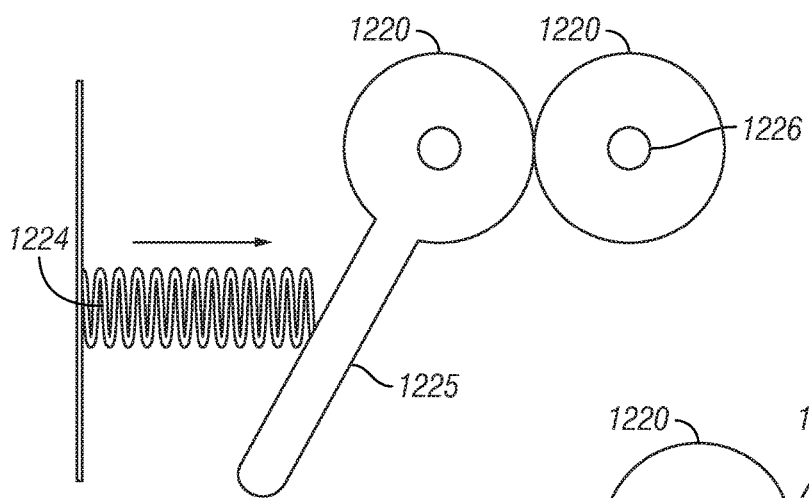
Figure 3D:
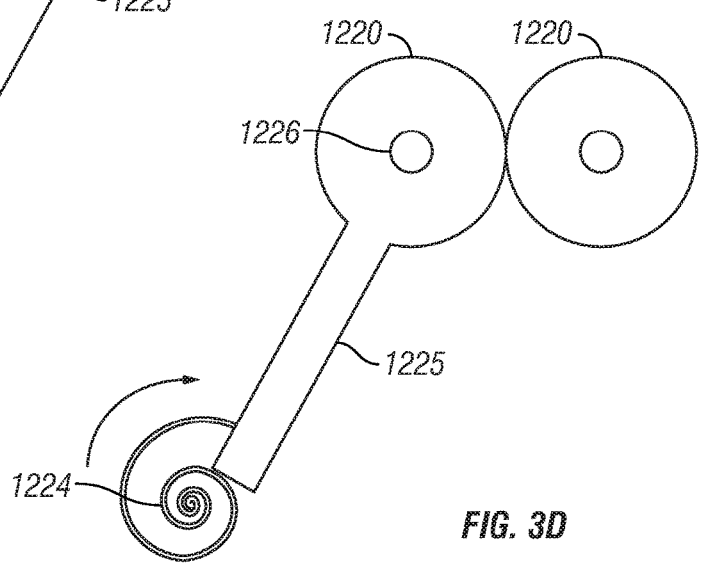

FIGS. 3B-3D show various embodiments of rollers 1220 with a spring 1224. FIG. 3B shows roller 1320 with spring 1224 in tension. FIG. 3C shows roller 1320 with spring 1224 in compression. FIG. 3D shows roller 1320 with spring 1224 in torsion. One or more rollers 1220 may be biased against another roller 1320. For example, two rollers 1220 may be biased against each other with a force of approximately 200 grams to 300 grams (N), or approximately 10 grams to 1000 grams (N). One or more rollers 1220 may biased against another roller 1220 with spring 1224. Spring 1224 may be in tension, compression, or torsion. Rollers 1220 may be biased against each other with a weight or any other suitable device. One or more rollers 1220 may be mounted on an arm 1225. One or more rollers 1220 may include bearings 1226.

Feeder 1200 may include one or more feed guides 1222. Feed guides 1222 may be placed before and/or after pinch point 1221 of rollers 1220. Feed guides 1222 may include any one or any combination of tubes, channels, grooves, holes, or any other suitable device. For example, feed guides 1222 may include a guide hole 1223 between spool holder 1210 and pinch point 1221. Feed guides 1222 may include floss exit hole 1311. Feed guides 1222 may be positioned between 1 mm and 50 mm from pinch point 1221. Feed guides 1222 are configured to guide floss through pinch point 1221 of rollers 1220.

Feeder 1200 may include at least one button 1230. Button 1230 may include a mechanical button and/or a touch-sensitive button such as a capacitive switch. Button 1230 may be coupled to housing 1100. Button 1230 may be coupled to front 1102 of housing 1100 and/or any other part of housing 1100. For a front 1102 of housing 1100 that is round or circular, first button 1231 and second button 1232 may be formed as two halves of a circle or a disc, and form at least a portion of front 1102 of housing 1100. Multiple buttons 1230 may be labeled to correspond to different users. For example, a first button 1231 may correspond to a first user, and a second button 1232 may correspond to a second user.

Button 1230 is configured to cause floss to be fed from spool holder 1210. Button 1230 may be configured to cause floss to be fed either through a user-powered mechanism or an electrically-powered mechanism. Alternatively, in addition to or in place of button 1230, floss dispenser 1000 may include any one or any combination of a motion sensor, a microphone configured to receive a voice and/or sound command, a lever, a crank, a knob, or any other suitable controls or devices for feeding floss. Alternatively, floss dispenser 1000 may include no buttons or mechanisms, and floss is fed by pulling floss from spool holder 1210 by hand.

Feeder 1200 may include a motor 1240. Motor 1240 may be connected to motor controller 1630. Motor 1240 may include any one or any combination of a DC motor, an AC motor, a stepper motor, or any other suitable actuator. Motor 1240 is coupled to one or more rollers 1220. Motor 1240 is configured to rotate rollers 1220. Motor 1240 may be configured to rotate rollers 1220 with sufficient speed to feed 18 inches of floss in approximately 0.1 seconds to 10 seconds, or approximately 3 seconds or less. Motor 1240 may have a speed of approximately 10 rpm to 20000 rpm.

Feeder 1200 may include gearing 1241. Gearing 1241 may couple motor 1240 to one or more rollers 1220. Gearing 1241 may be configured to gear down an output from motor 1240 to obtain a desired speed and/or torque at one or more rollers 1220. Gearing 1241 may include any one or any combination of a spur gear, a worm gear, a belt, or any other gearing.

Figure 3E:
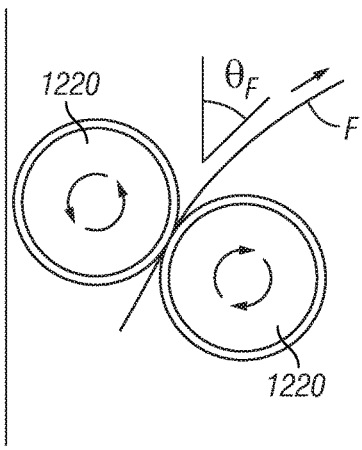
FIGS. 3E-3H show examples of how rollers 1220 may be arranged.
Figure 3F:
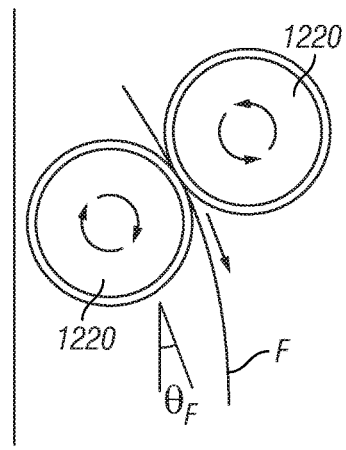
Figure 3G:
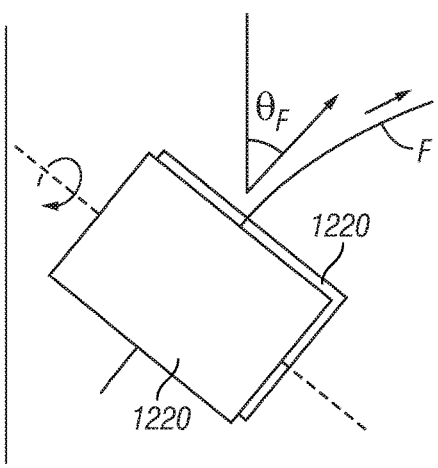
Figure 3H:
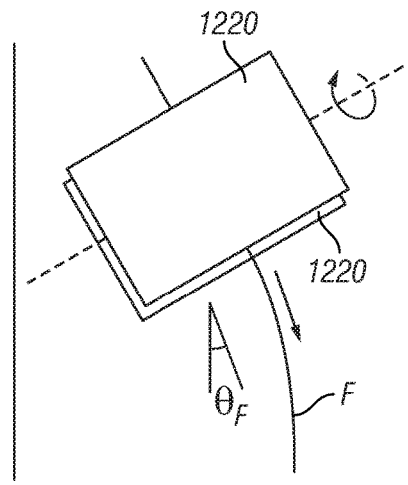

FIGS. 3E-3H show examples of how rollers 1220 may be arranged. FIGS. 3E-3F shows rollers 1220 arranged with their axes of rotation parallel to a vertical surface. By adjusting the positions of rollers 1220 with respect to each other, floss F may be fed at a desired feed angle $\Theta_F$. FIGS. 3G-3H shows rollers 1220 arranged with their axes of rotation at an angle to a vertical surface. By adjusting the angle of rollers 1220 relative to a vertical surface, floss F may be fed at a desired feed angle $\Theta_F$.

Housing 1100 may include a light ring 1107 and/or a light reflector 1108.

Figure 4A:
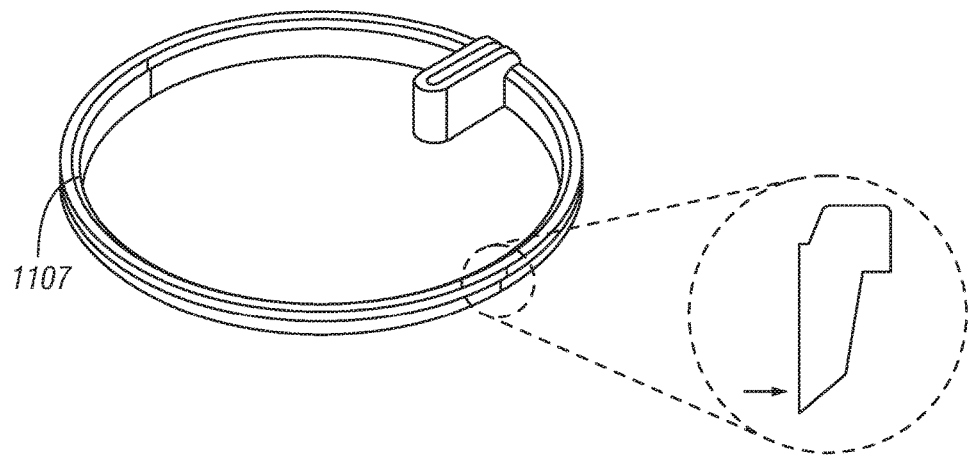
FIG. 4A shows one embodiment of light ring 1107.

FIG. 4A shows one embodiment of light ring 1107. Light ring 1107 may be coupled to front 1102 of housing 1100. Light ring 1107 may be coupled to a perimeter of front 1102 of housing 1100. Light ring 1107 may be coupled to any other part of housing 1100. Light ring 1107 may be circular. Light ring 1107 may be square or any other shape. One or more spout lights 1511 and/or one or more reminder lights 1521 may be arranged in a vicinity of light ring 1107. For example, one or more spout lights 1511 and/or one or more reminder lights 1521 may be positioned approximately 0.1 mm to 10 mm from light ring 1107. Light ring 1107 may be at least partially made of a semi-transparent and/or diffusive material. For example, light ring 1107 may be made of a semi-opaque plastic. Light ring 1107 is configured to diffuse light from one or more spout lights 1511 and/or one or more reminder lights 1521. Light ring 1107 may cause light from spout lights 1511 and/or reminder lights 1521 to be emitted more uniformly along light ring 1107. Light ring 1107 may increase an amount of light from spout lights 1511 and/or reminder lights 1521 that is emitted from housing 1100.

Figure 4B:
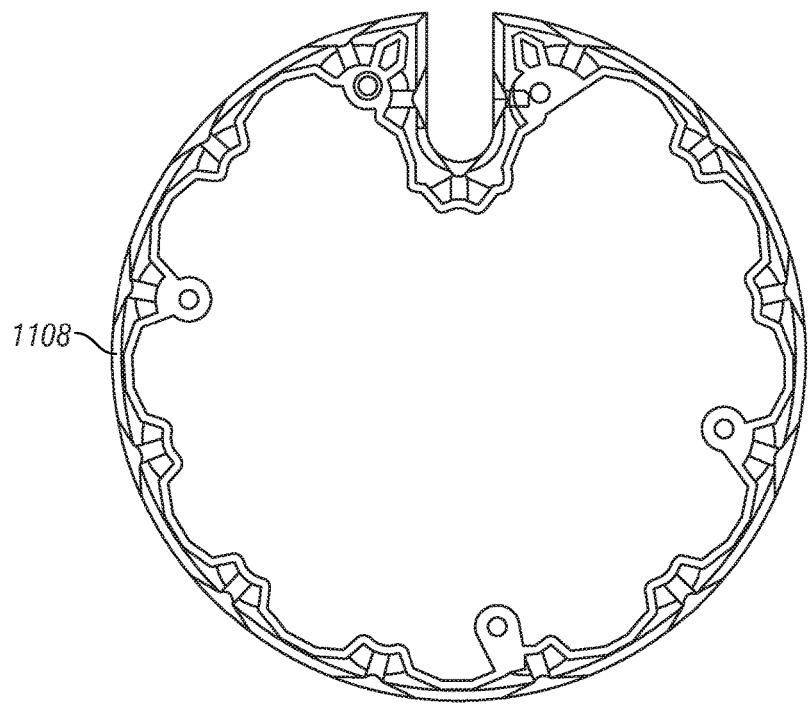
FIG. 4B shows one embodiment of light reflector 1108.

FIG. 4B shows one embodiment of light reflector 1108. Light reflector 1108 my be coupled to front 1102 of housing 1100. Light reflector 1108 may be coupled to a perimeter of front 1102 of housing 1100. Light reflector 1108 may be arranged next to light ring 1107. Light reflector 1108 may be coupled to any other part of housing 1100. One or more spout lights 1511 and/or one or more reminder lights 1521 may be arranged in a vicinity of light reflector 1108. For example, one or more spout lights 1511 and/or one or more reminder lights 1521 may be positioned approximately 0.1 mm to 10 mm from light reflector 1108. Light reflector 1108 may be at least partially made of a reflective material. Light reflector 1108 may include white and/or light-colored walls. Light reflector 1108 may include parabolic and/or hyperbolic walls. Light reflector 1108 may increase an amount of light from spout lights 1511 and/or reminder lights 1521 that is emitted from housing 1100.

FIGS. 5A-5F show one embodiment of a method of using floss dispenser 1000 in single user mode.

Figure 5A:
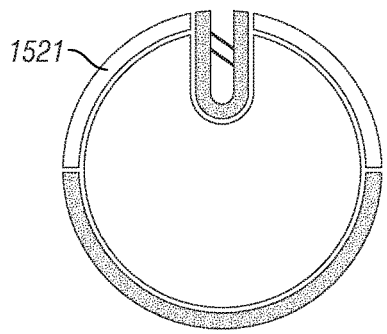
FIGS. 5A-5F show one embodiment of a method of using floss dispenser 1000 in single user mode.

FIG. 5A shows a reminder to floss. Reminder lights 1521 in an upper half of front 1102 of housing 1100 display a red frown. Speaker 1611 may give an audio reminder.

Figure 5B:
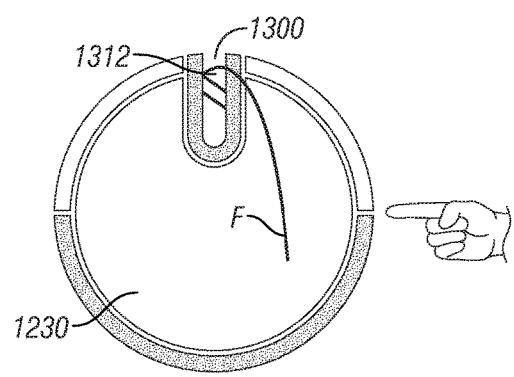

FIG. 5B shows feeding floss F to spout 1300. Floss F is fed to spout 1300 by pressing button 1230. Floss F may fall into cutter entry 1312.

Figure 5C:
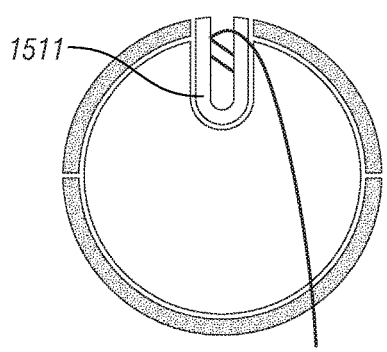

FIG. 5C shows an indication that floss F is ready to be cut. After floss F is fed to spout 1300, spout lights 1511 along edges of spout 1300 indicate that floss is ready to be cut.

Figure 5D:
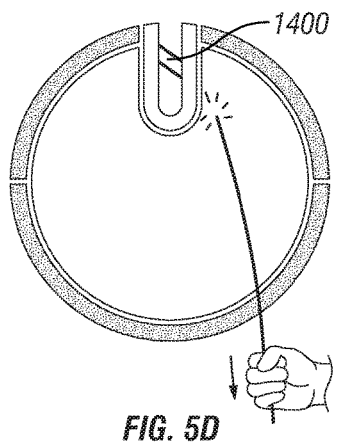

FIG. 5D shows cutting floss F. Floss F is cut by pulling floss F across cutter 1400. Floss F may be cut by pulling floss downward.

Figure 5E:
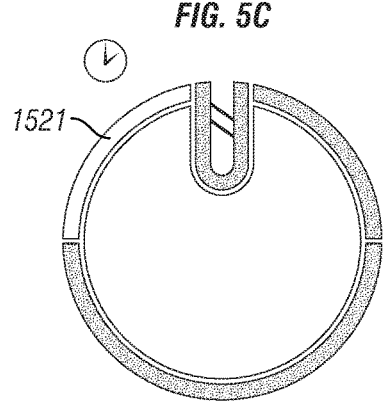

FIG. 5E shows an indication of a portion of a mouth to be flossed. Reminder lights 1521 in an upper left quarter of front 1102 of housing 1100 indicate that an upper left quadrant of the mouth is to be flossed. Then reminder lights 1521 in a lower left quarter of front 1102 of housing 1100 may indicate that a lower left quadrant of the mouth is to be flossed, and so on. Each quadrant is indicated for approximately 30 seconds, for a total of approximately 2 minutes for the entire mouth. Speaker 1611 may give audio instructions and/or play music.

Figure 5F:
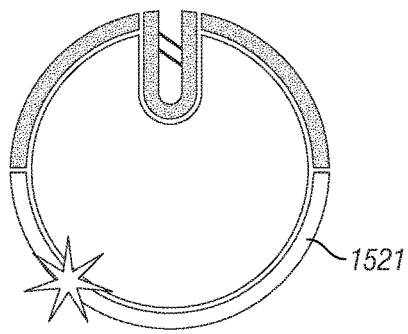

FIG. 5F shows an indication that a recommended amount of flossing time has elapsed. Reminder lights 1521 in a lower half of front 1102 of housing 1100 display a white smile. One or more reminder lights 1521 in a smile is lit more brightly than other reminder lights 1521 in the smile to resemble a "sparkle" in the smile. Speaker 1611 may play a completion melody. Reminder lights 1521 then turn off until the next reminder.

FIGS. 6A-6F show another embodiment of a method for using floss dispenser 1000 in dual user mode.

Figure 6A:
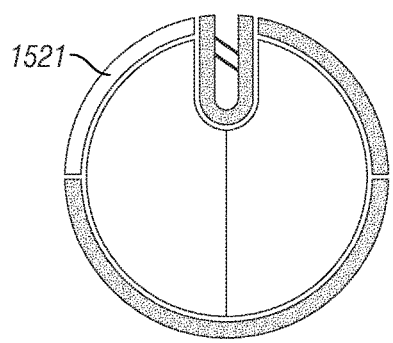
FIGS. 6A-6F show another embodiment of a method for using floss dispenser 1000 in dual user mode.

FIG. 6A shows a reminder to floss for a first user. Reminder lights 1521 along an upper left quarter of front 1102 of housing 1100 display half of a red frown. Speaker 1611 may give an audio reminder. Reminder lights 1521 along an upper right quarter of front 1102 of housing 1100 may be used to display reminders for a second user.

Figure 6B:
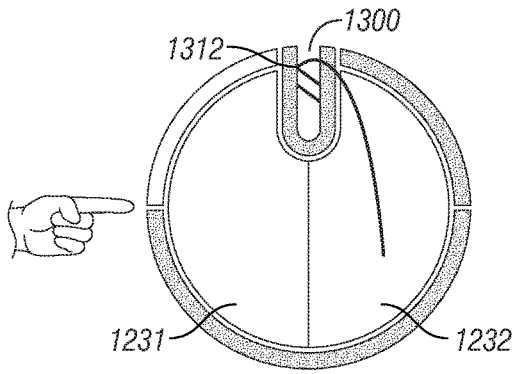

FIG. 6B shows feeding floss F to spout 1300. Floss F is fed to spout 1300 by pressing first button 1231. Floss F may fall into cutter entry 1312. Second button 1232 may be used for a second user.

Figure 6C:
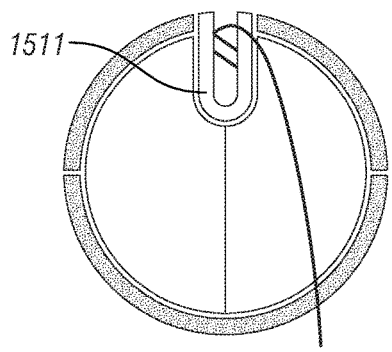

FIG. 6C shows an indication that floss F is ready to be cut. After floss F is fed to spout 1300, spout lights 1511 along edges of spout 1300 indicate that floss F is ready to be cut.

Figure 6D:
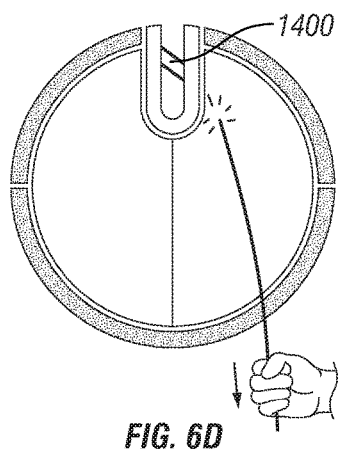

FIG. 6D shows cutting floss F. Floss F is cut by pulling floss across cutter 1400. Floss may be cut by pulling floss downward.

Figure 6E:
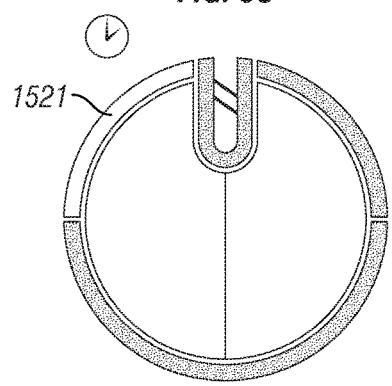

FIG. 6E shows an indication of a portion of a mouth to be flossed. Reminder lights 1521 in an upper left portion of front 1102 of housing 1100 indicate that an upper left quadrant of the mouth is to be flossed. Then reminder lights 1521 in a lower left portion of front 1102 of housing 1100 may indicate that a lower left quadrant of the mouth is to be flossed, and so on. Each quadrant is indicated for approximately 30 seconds, for a total of approximately 2 minutes for the entire mouth. Speaker 1611 may give audio instructions and/or play music.

Figure 6F:
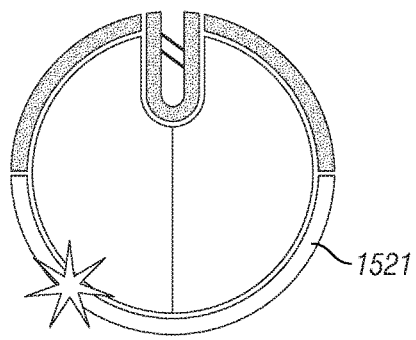

FIG. 6F shows an indication that a recommended amount of flossing time has elapsed. Reminder lights 1521 in a lower half of front 1102 of housing 1100 display a white smile. One or more reminder lights 1521 in a smile may be lit more brightly than other reminder lights 1521 in the smile to resemble a "sparkle" in the smile. Speaker 1611 may play a completion melody. Reminder lights 1521 then turn off until the next reminder.

Floss dispenser 1000 may be configured to record, store, and transmit data related to a user's flossing/brushing frequency, time spent in the shower, duration of faucet usage, number of times the toilet is flush, and general water usage. This may be done either via the cloud, by direct electronic connection of said processes to floss dispenser 1000, or by the use of radar and/or IR signaling to detect such actions. For example, running water in a shower exhibits a very distinct series of sounds that may be picked up by a microphone. Floss dispenser 1000 may use this microphone to record how long a user showers everyday; the same can be done for the number of times a person flushes the toilet or how long he/she keeps the faucet on.

Another set of functionalities that may be incorporated into the device is related to the analysis and monitoring of the user's oral and general health. For instance, floss dispenser 1000 may contain a cavity that captures a user's breath and analyzes it to detect bad breath or to assess oral microbiome health. Floss dispenser 1000 may also contain a built-in optical system that measures the "whiteness" of a user's teeth using reflectance spectroscopy. Additionally, physiological measurements such as electrocardiogram (EKG), heart rate, pulse oximetry (blood oxygenation), pH levels, and sugar levels may also be measured by incorporating the proper electrodes, optics, and/or chemistry. Floss dispenser 1000 may provide entertainment to a user. Videos, music and radio may be added to floss dispenser 1000.

Floss dispenser 1000 may have the capability to be connected to the cloud and/or the web via Wi-Fi, Bluetooth, or other means of connectivity. This connectivity may then allows floss dispenser 1000 to send collected data, be it flossing duration, water usage, or the user's physiology, to people and systems of interest. For instance, floss dispenser 1000 may send a monthly report to a user's phone, computer, or email detailing the average shower time, the total water use, the number of times the user flossed, or his/her day-to-day sugar levels. In addition, data may also be sent to a user's dentist, doctor, and/or insurance company for both health and logistical purposes. Data connectivity may further allow for cloud-based interactions such as ordering medications, floss refills, toothbrushes, or other products.

While the foregoing has been with reference to particular embodiments of the invention, it will be appreciated by those skilled in the art that changes in these embodiments may be made without departing from the principles and spirit of the invention.

What is claimed is:

1. A floss dispenser, comprising:
   a housing;
   a feeder coupled to the housing, the feeder configured to feed a length of floss from a spool of floss;
   a spout formed in the housing, the spout having a cutter entry and a cutter exit, the spout having a first wall and a second, opposing wall;
   a cutter coupled to the housing between the cutter entry and the cutter exit, the cutter having a blade extending partially from the first wall towards the second wall; and
   a guard coupled to the housing, the guard overlapping the cutter and configured to guide the length of floss to the cutter and away from a space between the second wall and the blade;
   wherein the feeder and the spout are configured to allow the length of floss to be pulled across the cutter at an angle of 0 to 90 degrees.

2. The floss dispenser of claim 1, wherein the housing is circular.

3. The floss dispenser of claim 1, wherein the housing is configured so that the housing combined with a reflection of the housing in a mirror resembles an hourglass.

4. The floss dispenser of claim 1, wherein the spout is at least partially formed in a front of the housing.

5. The floss dispenser of claim 1, wherein the spout is vertical.

6. The floss dispenser of claim 1, wherein the spout includes a floss exit hole configured to allow the length of floss to exit the housing.

7. The floss dispenser of claim 1, wherein the spout includes guide walls.

8. The floss dispenser of claim 7, wherein at least a portion of the guide walls are parallel.

9. The floss dispenser of claim 1, wherein the feeder and the spout are configured so that the length of floss falls under its own weight into the cutter entry.

10. The floss dispenser of claim 1, wherein the cutter entry is positioned above the cutter exit.

11. The floss dispenser of claim 1, wherein the length of floss is fed in an upward direction.

12. The floss dispenser of claim 11, wherein the length of floss is fed in an upward direction at an angle of 0 degrees to 90 degrees from vertical.

13. A floss dispenser, comprising:
a housing;
a feeder coupled to the housing, the feeder configured to feed a length of floss from a spool of floss;
a spout formed in the housing, the spout having a cutter entry and a cutter exit, the spout having a first wall and a second, opposing wall;
a cutter coupled to the housing between the cutter entry and the cutter exit, the cutter having a blade extending partially from the first wall towards the second wall; and
means for guiding the length of floss to the cutter and away from a space between the second wall and the blade, the means for guiding coupled to the housing;
wherein the feeder and the spout are configured to allow the length of floss to be pulled across the cutter at an angle of 0 to 90 degrees.

* * * * *